US005567408A

United States Patent [19]
Zamora

[11] Patent Number: 5,567,408
[45] Date of Patent: Oct. 22, 1996

[54] YIGSR PEPTIDE RADIOPHARMACEUTICAL APPLICATIONS

[75] Inventor: Paul O. Zamora, Puerta De Hierro, N.M.

[73] Assignee: RhoMed Incorporated, Albuquerque, N.M.

[21] Appl. No.: 483,447

[22] Filed: Jun. 6, 1995

Related U.S. Application Data

[60] Division of Ser. No. 998,910, Dec. 30, 1992, which is a continuation-in-part of Ser. No. 840,077, Feb. 20, 1992, Pat. No. 5,443,816.

[51] Int. Cl.$^6$ ............................. A61K 51/00; C07K 2/00; C07F 5/00
[52] U.S. Cl. ..................... 424/1.69; 530/300; 530/326; 530/327; 530/328; 530/329; 530/330; 534/10; 534/14; 534/15
[58] Field of Search ............................. 424/1.69, 9.1; 530/300, 326, 327, 328, 329, 330; 534/10, 14

[56] References Cited

U.S. PATENT DOCUMENTS

| | | | |
|---|---|---|---|
| 4,427,646 | 1/1984 | Olexa et al. | 424/1.1 |
| 4,479,930 | 10/1984 | Hnatowich | 424/1.1 |
| 4,668,503 | 5/1987 | Hnatowich | 424/1.1 |
| 4,732,864 | 3/1988 | Tolman | 436/547 |
| 4,822,606 | 4/1989 | Snyderman et al. | 424/188.1 |
| 4,877,868 | 10/1989 | Reno et al. | 530/390 |
| 4,986,979 | 1/1991 | Morgan, Jr. et al. | 424/1.1 |
| 5,039,662 | 8/1991 | Schasteen et al. | 514/17 |
| 5,078,985 | 1/1992 | Rhodes | 530/391.5 |
| 5,092,885 | 3/1992 | Yamada et al. | 623/11 |
| 5,102,990 | 4/1992 | Rhodes | 424/1.69 |
| 5,118,791 | 6/1992 | Burnier et al. | 530/326 |
| 5,190,920 | 3/1993 | Eyal et al. | 514/15 |
| 5,236,903 | 8/1993 | Saiki et al. | 514/12 |
| 5,328,840 | 7/1994 | Coller | 435/240.2 |
| 5,330,911 | 7/1994 | Hubbell et al. | 435/240.23 |
| 5,371,184 | 12/1994 | Rajagopalan et al. | 530/324 |
| 5,443,815 | 8/1995 | Dean et al. | 424/1.69 |
| 5,443,816 | 8/1995 | Zamora et al. | 424/1.69 |
| 5,460,785 | 10/1995 | Rhodes et al. | 424/1.49 |

FOREIGN PATENT DOCUMENTS

| | | |
|---|---|---|
| 2016235 | 11/1990 | Canada .................. 530/7.06 |
| 0196669 | 4/1986 | European Pat. Off. ........ C07K 17/06 |
| 0210684 | 7/1986 | European Pat. Off. ........ A61K 49/02 |
| 0250013 | 5/1987 | European Pat. Off. ........ C07F 13/00 |
| 0359347 | 3/1990 | European Pat. Off. . |
| WO92/13572 | 2/1992 | European Pat. Off. ........ A61K 9/02 |
| 2225579 | 6/1990 | United Kingdom . |
| PCT/GB90/00933 | 12/1990 | WIPO ............. C07K 5/08 |
| WO91/01144 | 7/1991 | WIPO . |
| PCT/US92/00757 | 8/1992 | WIPO ............. A61K 49/02 |
| 9312819 | 7/1993 | WIPO . |
| 9323085 | 11/1993 | WIPO . |
| 9325244 | 12/1993 | WIPO . |
| 9501188 | 1/1995 | WIPO . |

OTHER PUBLICATIONS

Sandrock, B., "Kinetics of I.V. Injected 1–131–Labeled Laminin–$C_1$–Fragmet in Normal and Tumor–Bearing Nude Mice," Proceedings of the AACR, vol. 30, Abstract No. 390 (1989).

Liotta, Lance A., "Laminin Receptors on Human Breast Carcinoma: Role in Invasion of the Extracellular Matrix", Understanding Breast Cancer: Clinical and Laboratory Concepts, Rich, N, et al (eds). pp. 87–97 (1983).

Zamora, P. O., et al., "A Second Tc–99m Binding Site In IgG. Is Related To Distadine Groups," J. Nucl. Med., vol. 33, No. 5, (1992), Abstract No. 86.

Swanson, D., et al "Laminin Peptide Fragments for Malignant Tumor Detection", Proc. of 40th Ann. Meet., *Journal of Nuclear Medicine*, vol. 34, No. 5, p. 231P (May 1993).

Buchanan, M. R., "Mechanisms of Pathogenesis of Arterial Thrombosis: Potential Sites of Inhibition by Therapeutic Compounds", *Sem. Thrombosis and Hemostasis*, vol. 14, pp. 33–40 (1988).

Hynes, R. O., "Integrins: Versatility, Modulation, and Signalling in Cell Adhesion", *Cell*, vol. 69, pp. 11–25 (1992).

Ill, Charles R., et al., "Adhesion of Platelets to Laminin in the Absence of Activation", *J. of Cell Biol.*, vol. 99, pp. 2140–2145 (1984).

Imura, Yoshimi, et al., "Antithrombotic Properties of L–Cysteine . . . ",*Blood*, vol. 80, No. 5, pp. 1247–1253 (1992).

Knight, L. C., et al., "Thrombus Imaging with Tc–99m Synthetic Peptides Reactive with Activated Platelets", *J. Nucl. Med.*, vol. 31, p. 757 (Abstract) (1990).

Shah, V. O., et al., "In Vitro Studies with the Platelet–Reactive Antibody 50H.19 and Its Fragments", *Thrombosis Research*, vol. 58, pp. 493–504 (1990).

Som, P., et al., "Radioimmunoimaging of Experimental Thrombi in Dogs Using Tc–99m Labeled Monoclonal Antibody Fragments Reactive with Human Platelets", *J. Nucl. Med.*, vol. 27, pp. 1315–1320 (1986).

Sonnenberg, A., et al., "Isolation of Alpha6Beta1 Integrins from Platelets and Adherent Cells by Chromatography on Mouse Laminin Fragment E8 and Human Laminin Pepsin Frament", *Exp Cell Res.*, vol. 197, pp. 234–244 (1991).

Tandon, N. M., et al., "Interactionof Human Platelets with Laminin and Identification of the 67 kDa Laminin Receptor on Platelets", *Biochem J.*, vol. 274, pp. 535–542 (1991).

Yamada, K. M., et al., "Adhesive Recognition Sequences", *J. Biol. Chem.*, vol. 266, pp. 2809–2812 (1992).

(List continued on next page.)

Primary Examiner—John Kight
Assistant Examiner—Dameron L. Jones
Attorney, Agent, or Firm—Deborah A. Peacock; David P. Hegge

[57] ABSTRACT

Peptides containing a biological-function domain which includes the sequence Tyr-Ile-Gly-Ser-Arg (YIGSR) and a medically useful metal ion-binding domain are labeled with medically useful metal ions for use in a variety of diseases and pathologic conditions, and particularly for diagnosis and treatment of thrombosis and other diseases and conditions.

12 Claims, No Drawings

OTHER PUBLICATIONS

Pimm, M. V., et al., "In labelling of a branched polypeptide drug carrier with a poly(L–lysin) backbone,"Int'l J. Pharm., vol. 79 (1992) pp. 77–80.

Zamora, P. O., et al., "Lung Uptake of $^{99m}$Tc–Laminin Peptide PA22–2 Is Decreased in Emphysema and Increased in Tumored Lung", Abstract, J. Nucl. Med., vol. 34, No. 5, (1993), Abstract No. 1133.

Babich et al (1993). Technetium –99m labeled hydra zino nicotinamide derivatized chemotactic peptide analog for imaging focal sites of bacterial infection. J. Nucl. Med., vol. 34, No. 11, pp. 1964–1974.

Zamora et al (1993). Biological distribution of 99m–Tc labeled YIGSR and IKVAV laminin peptides in rodents: 99m–Tc–IKVAV peptide localizes to the lungs. Biochim. Biophys. Acta., vol. 1182, No. 2, pp. 197–204.

Zamora et al (1992). Imidazdes as Well as Thioates in Proteins Bind Technetium –99m. Bioconjugate Chemstry, vol. 3, No. 6, pp. 493–498.

Murata et al (1989). Int. J. Biol. Macromol., vol. 11, No. 2, pp. 97–99. Inhibitory effect of a Synthetic polypeptide, poly(Tyr–Ile–Gly–Ser–Arg), on metastatic formation of malignant tumor cells.

YIGSR PEPTIDE RADIOPHARMACEUTICAL APPLICATIONS

LICENSE RIGHTS

The U.S. Government has a paid-up license in this invention and the right in limited circumstances to require the patent owner to license others on reasonable terms as provided for by the terms of Small Business Innovative Research Grants No. 2 R44 CA50877 and 1 R43 CA58136 awarded by the National Institutes of Health, Department of Health and Human Services.

CROSS-REFERENCE TO RELATED APPLICATIONS

This is a divisional of application Ser. No. 07/998,910 filed on Dec. 30, 1992, Ser. No. 07/998,910 was a continuation-in-part application of U.S. patent application Ser. No. 07/840,077, filed Feb. 20, 1992, now U.S. Pat. No. 5,443,816 issued Aug. 22, 1995 entitled *Peptide-Metal Ion Pharmaceutical Preparation and Method;* and is related to U.S. Pat. No. 5,102,990, entitled *Direct Radiolabeling of Antibodies and Other Proteins with Technetium or Rhenium;* U.S. Pat. No. 5,078,985, entitled *Radiolabeling Antibodies and Other Proteins with Technetium or Rhenium by Regulated Reduction;* U.S. patent application 07/815,122, entitled *Composition for Radiolabeling Antibodies and Other Proteins by Regulated Reduction,* later abandoned; U.S. patent application 07/815,123, entitled *Method for Radiolabeling Antibodies and Other Proteins by Regulated Reduction,* later abandoned; U.S. patent application 07/816,476, now U.S. Pat. No. 5,346,687 entitled *Direct Radiolabeling of Antibody Against Stage Specific Embryonic Antigen for Diagnostic Imaging;* U.S. patent application 07/816,477, now U.S. Pat. No. 5,460,785 entitled *Direct Labeling of Antibodies and Other Proteins with Metal Ions;* and U.S. patent application 07/840,076, entitled *Leukostimulatory Agent for In Vivo Leukocyte Tagging;* U.S. patent application 07/864,470, now U.S. Pat. No. 5,277,893 entitled *Direct Radiolabeling of Substrates Containing Monosulfides or Disulfide Bonds with Radionuclides;* and a U.S. patent application Ser. No. 07/998,820 filed concurrently herewith entitled *IKVAV Peptide Radiopharmaceutical Applications;* the teachings of all of the foregoing which are incorporated herein by reference.

BACKGROUND OF THE INVENTION

1. Field of the Invention (Technical Field)

This invention relates to peptide-based metal ion-labeled compositions for use as pharmaceuticals, and particularly radiopharmaceuticals, for diagnostic imaging and therapeutic applications, and more particularly for in vivo labeling of platelets for localization and detection of thrombosis, and detecting and treatment of other diseases and conditions.

2. Description of the Related Art, Including Information Disclosed under 37 C.F.R. Sections 1.97–1.99 (Background Art)

The use of biologically active peptides, which are peptides which bind to specific cell surface receptors, have received some consideration as radiopharmaceuticals. Canadian Patent Application 2,016,235, Labeled *Chemotactic Peptides to Image Focal Sites of Infection or Inflammation,* teaches a method of detecting a site of infection or inflammation, and a method for treating such infection or inflammation, by administration of a labeled or therapeutically-conjugated chemotactic peptide. In that application, the chemotactic peptides are chemically conjugated to DTPA and subsequently labeled with $^{111}$In. The utility of DTPA chelates covalently coupled to polypeptides and similar substances is well known in the art. Hnatowich, DJ, U.S. Pat. Nos. 4,479,930 and 4,668,503. Other bifunctional chelates for radiolabeling peptides, polypeptides and proteins are well known in the art. Other biologically active peptides described include those disclosed by Olexa SA, Knight LC and Budzynski AZ, U.S. Pat. No. 4,427,646, *Use of Radiolabeled Peptide Derived From Crosslinked Fibrin to Locate Thrombi In Vivo,* in which iodination is discussed as a means of radiolabeling. In Morgan CA Jr and Anderson DC, U.S. Pat. No. 4,986,979, *Imaging Tissue Sites of Inflammation,* use of chelates and direct iodination is disclosed. In Tolman GL, U.S. Pat. No. 4,732,864, *Trace-Labeled Conjugates of Metallothionein and Target-Seeking Biologically Active Molecules,* the use of metallothionein or metallothionein fragments conjugated to a biologically active molecule, including peptides, is disclosed. The previous methods all employ some conjugation means with a bifunctional chelator in order to effectuate labeling with a radionuclide or other medically useful metal ion, such as a paramagnetic contrast agent. The only exception involves radioiodination; the iodine labeling of proteins or peptides containing tyrosine or histidine residues is well known, for example, by the chloramine-T, iodine monochloride, Iodogen or lactoperoxidase methods.

Under homeostatic conditions, platelets circulate as disc shaped cells that do not interact with other circulating blood cells or vascular endothelium (Buchanan MR: Mechanisms of pathogenesis of arterial thrombosis: potential sites of inhibition by therapeutic compounds, *Sem Thrombosis and Hemostasis* 14(1988) 33–40). The release of adhesive and coagulant agents associated with platelet activation is held in check by high intraplatelet, and possibly vascular endothelium, levels of cAMP.

Upon injury, platelets rapidly attach a) to dysfunctional or detached endothelial cells and b) to the underlying basement membrane and tissues. Differences in platelet response, correlating to the degree of injury, are due in part to differences in the vessel wall composition of the molecules to which the platelets adhere. For example, type I and III collagens, which are typically associated with smooth muscle cells, promote platelet adhesion, aggregation, and release. In contrast, types IV and V collagens, typically associated with the endothelium, facilitate platelet adhesion but do not generally cause platelet activation.

Platelet-mediated thrombosis is a major pathogenetic mechanism in thrombogenesis and reocclusion after successful thrombolytic therapy, and consequently platelets are frequently used as vehicles for localization of thrombi. Additionally, suppression of platelet aggregation is a frequent target for prevention of blood vessel occlusion or reocclusion. There are a number of clinical conditions in which there are platelet accumulations; these include venous thrombosis, arterial thrombosis, left ventricular thrombosis, pulmonary embolism, inflammatory response secondary to myocardial infarction, endocarditis, bypass graft occlusion, aneurysms, prosthetic arterial graft platelet accumulation or occlusion, cerebral embolism or hemorrhage, traumatic injury with hemorrhage, gastrointestinal hemorrhage, and thrombosis secondary to catheters and other implanted devices.

A variety of diagnostic modalities have been used for conditions involving platelet accumulation. These include contrast venography, impedance plethysmography, and $^{125}$I- fibrinogen uptake for venous thromboembolism; $^{111}$In-labeled platelets for a variety of conditions involving platelet accumulation; and, pulmonary angiography, perfusion lung scanning using $^{99m}$Tc-human macroaggregated albumin, and ventilation-perfusion lung scanning with radioactive gases or aerosols for pulmonary embolism. Each of these modalities presents serious limitations, and has less than desirable efficacy. $^{111}$In-labeled platelets is the only modality which yields a reliable direct measure of platelet accumulation; however, this method suffers serious limitations, including technical difficulties in ex vivo labeling. In addition, since with $^{111}$In-labeled platelets the labeling is performed ex vivo, and the platelets reinjected and allowed to accumulate before imaging, this method does not provide a measure of existing platelet accumulation. Thus, no commonly used method allows for direct detection of existing platelet accumulation within the body.

Peptides containing the adhesive sequence RGD are under active investigation as anti-thrombotic agents (Imura Y, Stassen J-M, Dunting S, Stockmans F, and Collen D: Antithrombotic properties of L-cysteine, N-(mercaptoacetyl)-D-Tyr-Arg-Gly-Asp-sulfoxide (G4120) in hamster platelet-rich femoral vein thrombosis model, *Blood* 80(1992) 1247–1253). Knight et al. (Knight LC, Radcliffe R, Kollman M, Dasika V, Wikander R, Mauer AH, Rodwell JD, and Alvarez V: Thrombus imaging with Tc-99m synthetic peptides reactive with activated platelets. *J Nucl Med* 31(1990) 757 (abstract)) have reported on the use of $^{99m}$Tc-synthetic peptide-metallothionein complexes which bind to the platelet glycoprotein IIb/IIIa complex to image fresh thrombi in jugular veins. However, peptides which target the glycoprotein IIb/IIIa complex are known to adversely affect platelet aggregation, and consequently a radiopharmaceutical based on such an approach would be expected to have severe dose limitations.

In addition to peptides, radiolabeled monoclonal antibodies specific for platelet-related antigens have been studied as diagnostic radiopharmaceuticals. (Shah VO, Zamora PO, Mills SL, Mann PL, and Comp PC: In vitro studies with the platelet-reactive antibody 50H.19 and its fragments. *Thrombosis Research* 58(1990) 493–504; Som P, Oster ZH, Yamamoto K, Sacker DF, Brill AB, Zamora PO, Newell KD, and Rhodes BA: Radioimmunoimaging of experimental thrombi in dogs using Tc-99m labeled monoclonal antibody fragments reactive with human platelets. *J Nucl Med* 27(1986) 1315–1320).

Laminin is a basement membrane glycoprotein ($M_r$=900,000) which has various biological activities including promoting cell attachment, growth, and differentiation. A typical laminin molecule consists of three polypeptide chains, A (440 kd), B1 (200 kd), and B2 (220 kd), that are linked by disulfide bonds to form an asymmetric cross-structure. Multiple, distinct adhesive sequences in laminin appear to mediate specific biological functions, and bind to distinct cell surface receptors (Hynes RO: Integrins: versatility, modulation, and signaling in cell adhesion, *Cell* 69(1992) 11–25; Yamada KM: Adhesive recognition sequences, *J Biol Chem* 266(1992) 2809–2812).

Integrin-type receptors on platelets (glycoprotein Ib, the glycoprotein IIb/IIIa complex and glycoprotein IV) have been identified as the major adhesion receptors in platelets, but these glycoproteins do not appear to play a role in the interaction of platelets with the intact laminin molecule (Tandon NN, Holland EA, Kralisz U, Kleinman HK, Robey FA, and Jamieson GA: Interaction of human platelets with laminin and identification of the 67 kDa laminin receptor on platelets, *Biochem J* 274(1991) 535–542). However, platelets do bind to laminin peptide fragments via these receptors (Sonnenberg A, Gehlsen KR, Aumailley M, and Timpl R: Isolation of $\alpha 6\beta 1$ integrins from platelets and adherent cells by affinity chromatography on mouse laminin fragment E8 and human laminin pepsin fragment, *Exp Cell Res* 197(1991) 234–244), suggesting that normally these sites in laminin are cryptic for platelets. One non-integrin platelet receptor for laminin is a 67 kDa receptor which binds to laminin-derived peptide sequences containing Tyr-Ile-Gly-Ser-Arg (YIGSR) (Tandon et al., supra). This platelet receptor appears to play an important role in the interaction of platelets with the intact laminin molecule. Platelet adherence to laminin via this receptor does not in itself result in platelet activation (Ill CR, Engvall E, and Ruoslahti E: Adhesion of platelets to laminin in the absence of activation. *J Cell Biol* 99(1984) 2140–2145).

Peptides containing the YIGSR peptide sequence have been proposed as anti-metastatic agents. Yamada Y, Graf JO, Iwamoto Y, Rober F, Kleinman HK, Sasaki M and Martin GR, U.S. Pat. No. 5,092,885, *Peptides with Laminin Activity;* Schasteen CS, U.S. Pat. No. 5,039,662, *Peptide with Anti-Metastatic Activity.* These patents involve longer sequences containing the YIGSR peptide sequence, as well as acylated YIGSR peptide sequences.

SUMMARY OF THE INVENTION (Disclosure of the Invention)

In accordance with the present invention, a method of performing an administrative procedure in a patient, which may be either diagnostic or therapeutic is provided. In this method, a medically useful metal ion-labeled peptide comprising a peptide sequence comprising the sequence YIGSR and a medically useful metal ion, is prepared and an effective amount administered to the patient. In one embodiment, the peptide is a peptide comprising the sequence CDPGYIGSR.

The method is most commonly employed for diagnostic procedures, with the preferred diagnostic procedure comprising imaging by metal ion detection means. Representative metal ion detection means include gamma scintigraphy, specific photon emission computerized tomography, positron emission tomography and magnetic resonance imaging. A variety of metal ions may be employed, including ionic elements of iron, cobalt, nickel, copper, zinc, arsenic, selenium, molybdenum, technetium, ruthenium, palladium, silver, cadmium, indium, antimony, rhenium, osmium, iridium, platinum, gold, mercury, thallium, lead, bismuth, polonium and astatine. These ionic elements will most generally be radioactive, paramagnetic or superparamagnetic.

The diagnostic procedure will frequently involve detection of sites of platelet accumulation. A variety of conditions can be diagnosed by detection of sites of platelet accumulation, including various types of thrombosis, including venous thrombosis, arterial thrombosis, and left ventricular thrombosis, pulmonary embolism, inflammatory response secondary to myocardial infarction, endocarditis, bypass graft occlusion, aneurysms, prosthetic arterial graft platelet accumulation, prosthetic arterial graft platelet occlusion, cerebral embolism, cerebral hemorrhage, traumatic injury with hemorrhage, gastrointestinal hemorrhage, and thrombosis secondary to catheters and other implanted devices. The diagnostic procedure may also involve detection of carcinomas, both primary carcinomas and metastatic carcinomas.

Im employing the method, the medically useful metal ion-labeled peptide can further comprises a chelating agent, whereby the medically useful metal ion is bound to the peptide via the chelating agent. The chelating agent can be a bifunctional agent.

The administration of the medically useful metal ion-labeled peptide is most commonly parenteral. It will generally be intravenous injection, but may also be intradermal, subcutaneous, intramuscular or intraperitoneal.

The medically useful metal ion-labeled peptide can further include a metal ion-binding domain, such that the medically useful metal ion-labeled peptide comprises the sequence YIGSR and a metal ion-binding domain, whereby the linked medically useful metal ion is bound to the peptide via the metal ion-binding domain. Thus, the peptide combination comprising the sequence YIGSR and a metal ion-binding domain can be selected from the group $(R_1)$-$[Y_1]_n$-$(R_2)$,
$(R_1)$-$[Y_1$-$(R_2)$-$Y_1]_n$-$(R_3)$, and
$(R_1)$-$[Y_1$-$(R_2)$-$Y_2]_n$-$(R_3)$ wherein the metal ion-binding domain comprises a member selected from the group consisting of $[Y_1]_n$, $[Y_1$-$(R_2)$-$Y_1]_n$ and $[Y_1$-$(R_2)$-$Y_2]_n$ wherein n is a number between 1 and about 6, and $Y_1$ and $Y_2$ are amino acids comprising at least one element selected from the group consisting of sulfur, nitrogen or oxygen which is available or can be made available for binding to metal ions;

the peptide sequence YIGSR comprises at least one member selected from the group consisting of $R_1$, $R_2$ and $R_3$ and further comprises an amino acid sequence containing from 5 to about 20 amino acids; and those portions of $R_1$, $R_2$ and $R_3$ not comprising the peptide sequence YIGSR each comprise an amino acid sequence containing from 0 to about 20 amino acids.

In those methods employing a metal ion-binding domain, that domain may comprises at least one amino acid sequence selected from the group consisting of cysteine, cystine, histidine, penicillamine, deacylated methionine, lysine, arginine, aspartic acid, glutamic acid and tyrosine. Most commonly, the metal ion-binding domain will be selected from the group $[Cys]_n$,
$[Cys$-$(R_2)$-$Cys]_n$,
$[Cys$-$(R_2)$-$Pen]_n$,
$[His$-$(R_2)$-$Cys]_n$,
$[His$-$(R_2)$-$Pen]_n$,
$[His]_n$, and
$([His$-$(R_2)$-$His]_n$ wherein n is a number between 1 and about 6; and $R_2$ is an amino acid sequence containing from 1 to about 20 amino acids.

The present invention also provides a peptide-based pharmaceutical composition suitable for administration to a patient. The composition, which may be lyophilized, includes a peptide comprising, in part, a biological-function domain which comprises the peptide sequence YIGSR and further comprising, in part, a medically useful metal ion-binding domain. The peptide-based pharmaceutical composition may further comprise a metal ion labeling agent, and may also further comprise a medically useful metal ion. The peptide is selected from the group consisting of $(R_1)$-$[Y_1]_n$-$(R_2)$,
$(R_1)$-$[Y_1$-$(R_2)$-$Y_1]_n$-$(R_3)$, and
$(R_1)$-$[Y_1$-$(R_2)$-$Y_2]_n$-$(R_3)$ wherein the medically useful metal ion-binding domain comprises a member selected from the group consisting of $[Y_1]_n$, $[Y_1$-$(R_2)$-$Y_1]_n$ and $[Y_1$-$(R_2)$-$Y_2]_n$ in which n is a number between 1 and about 6 and $Y_1$ and $Y_2$ are amino acids comprising at least one element selected from the group consisting of sulfur, nitrogen or oxygen which is available or can be made available for binding to metal ions;

the biological-function domain comprising the peptide sequence YIGSR further comprises at least one member selected from the group consisting of $R_1$, $R_2$ and $R_3$; and those portions of $R_1$, $R_2$ and $R_3$ not comprising the biological-function domain comprising the peptide sequence YIGSR each comprise an amino acid sequence containing from 0 to about 20 amino acids.

One peptide which may be employed in this peptide-based pharmaceutical composition is a peptide comprising the sequence CDPGYIGSR.

The medically useful metal ion-binding domain of the peptide-based pharmaceutical composition may include amino acid sequences containing cysteine, cystine, histidine, penicillamine, deacylated methionine, lysine, arginine, aspartic acid, glutamic acid and tyrosine. Specific medically useful metal ion-binding domains include the following:

$[Cys]_n$,
$[Cys$-$(R_2)$-$Cys]_n$,
$[Cys$-$(R_2)$-$Pen]_n$,
$[His$-$(R_2)$-$Cys]_n$,
$[His$-$(R_2)$-$Pen]_n$,
$[His]_n$, and
$([His$-$(R_2)$-$His]_n$ wherein n is a number between 1 and about 6; and $R_2$ is an amino acid sequence containing from 1 to about 20 amino acids.

The metal ion labeling agent of the peptide-based pharmaceutical composition can be a stannous ion agent, which may be present in a solution comprising alkali metal tartrate. The solution may also comprise dicarboxylic acids, such as phthalate, tartrate or citrate. The stannous ion agent itself may be stannous tartrate, stannous glucoheptonate, stannous gluconate, stannous phosphonate, stannous chloride, or stannous fluoride.

Accordingly, it is an object of the present invention to provide for pharmaceutically useful peptides comprising a biological-function domain containing the sequence YIGSR and a linked metal ion.

It is a further object of the present invention to provide a means whereby thrombosis and other diseases and lesions characterised by concentrations of platelets can be diagnosed and treated.

It is a further object of the present invention to provide a means whereby metal ion-binding domains can be directly synthesized or genetically introduced into a peptide comprising a biological-function domain containing the sequence YIGSR, thereby allowing labeling without the necessity of conjugation to bifunctional chelators.

Another object of the present invention to provide a method for performing a diagnostic procedure by administration of a metal ion-labeled peptide composed of a biological-function domain containing the sequence YIGSR and a metal ion-binding domain.

Another object of the present invention is to provide a method for the direct labeling of peptides comprising a biological-function domain including the sequence YIGSR, and which peptides further comprise amino acid sequences containing amino acids with sulfur, nitrogen or oxygen which is available or can be made available for binding metal ions, such as cysteine, histidine or penicillamine, or some combination thereof.

It is a further object of the present invention to provide a method to label peptides containing a biological-function domain including the sequence YIGSR with medically useful metal ions without loss of the biological function of the peptide due to the labeling process.

Another object of the present invention is to provide a method and product which permits labeling to be accomplished by the end user using a single vial, containing a peptide with a biological-function domain comprising at least the sequence YIGSR and a medically useful metal ion binding domain and a metal ion labeling agent, which method requires only a single step to accomplish labeling, being the introduction of the medically useful metal ion.

Other objects, advantages and novel features, and further scope of applicability of the present invention will be set forth in part in the detailed description to follow and in part will become apparent to those skilled in the art upon examination of the following, or may be learned by practice of the invention. The objects and advantages of the invention may be realized and attained by means of the instrumentalities and combinations particularly pointed out in the appended claims.

DETAILED DESCRIPTION OF THE PREFERRED EMBODIMENTS OF THE INVENTION (BEST MODES FOR CARRYING OUT THE INVENTION)

Using the methods of this invention, peptides with a biological-function domain comprising at least the sequence YIGSR and a linked radiolabel provide materials useful for in vivo diagnostic applications, particularly for diagnostic imaging of thrombosis and other conditions characterized by accumulation of platelets. Preferably, the peptide comprises a biological-function domain comprising at least the sequence YIGSR and a metal-ion binding domain comprising metal ion binding sequences which can be coupled directly with metal ions. The peptides can be prepared in a format providing a labeling kit which can, in turn, be used to prepare a metal ion-peptide complex for in vivo use. It is also possible to provide for labeling of a peptide with the biological-function domain with a metal ion in vivo, such as through use of a peptide-avidin complex, which is injected in vivo, followed by a biotin-metal ion complex inject in vivo, resulting in formation of an in vivo peptide-avidin-biotin-metal ion complex. The peptides of this invention preferably contain:
a) biological-function domains comprising at least the sequence YIGSR, and
b) metal ion-binding domains which can complex with medically useful metal ions.

The terms "bind," "binding," "complex," and "complexing," as used throughout the specification and claims, are intended to cover all types of physical and chemical binding, reactions, complexing, attraction, chelating and the like.

The biological-function domain of the preferred peptide is defined in the specification and claims as a sequence of the amino acids Tyr-Ile-Gly-Ser-Arg (YIGSR single amino acid code), and optionally amino acids in addition to YIGSR. The peptide of this invention thus preferably includes the sequence YIGSR, which may be repeated one or more times. Usually, within the indicated sequences, there may be mutations, including deletions, insertions or substitutions. For the most part, substitutions will be conservative, in which amino acids having substantially the same conformation and polarity may be employed. The peptides may use L-amino acids, or one or more of the amino acids may be substituted by D-amino acids (D-stereoisomer). Particularly, one or more alanines may be substituted. In the alternative, terminal amino acids may be employed having unnatural chirality. The peptide may also include a terminal amide or a terminal acylated amino acid, particularly acetylated or alkylated, particularly methylated, amino acids. Where a cysteine provides the metal-ion binding domain at the N-terminus, the cysteine may be alkylated or unsubstituted on the mercaptan group.

The metal ion-binding domain of the peptide is defined in the specification and claims as a sequence of one or more amino acids containing sulfur, nitrogen or oxygen which is available for binding or can be made available for binding to metal ions. Sulfur-containing amino acids include primarily cysteine (Cys), cystine (Cys-Cys) and penicillamine (Pen), although deacylated methionine (Met), and other amino acids, may also be used. Useful nitrogen-containing amino acids include primarily histidine (His), but under certain conditions lysine (Lys) and arginine (Arg), which have $pK_a$ values of 10.0 and 12.0, and other amino acids, may also be employed. In addition, the terminal amino group of peptides may also be employed. Useful oxygen-containing amino acids include aspartic acid (Asp), glutamic acid (Glu) and tyrosine (Tyr), as well as the terminal carboxyl group of peptides and other amino acids. The amino acid sequences most usefully employed will include one or more Cys, one or more His, or a combination of Cys and His. Pen, which is an analogue of Cys, may be directly substituted for any given Cys. Cys may be present in the peptide as a disulfide in the form of cystine. The metal ion-binding domain may employ L-amino acids, or one or more of the amino acids may be substituted by D-amino acids (D-stereoisomer). The metal ion-binding domains may occur once or multiple times in any given peptide, and may occur in any combination. The metal ion-binding domain and the biological-function domain may overlap.

The metal binding sequences as found in the peptides of this invention may be stabilized by the addition of a positively-charged transition metal ion of Zn, Cu, Sn, Co, or Ni, and the like, selected to have a low order of binding strength. Through a replacement reaction, the transition metal ion replaces the H ion of the thiolate, imidazole or carboxyl group. The divalent ions of zinc and tin are thought to be particularly attractive. Some transition metals can simultaneously be used to reduce disulfide bridges and stabilize the metal binding sequences, such as Sn (II), which is particularly useful with cystine formations. In any case, the transition metals are weakly associated with the peptide.

The positively-charged transition metal ions are introduced to the peptide in an aqueous solution containing an appropriate buffer. The buffer may consist of dicarboxylic acids (tartrate, phthalate, citrate), amino acids (glycine, di-glycine, tri-glycine), borate or the like. For radiolabeling in acidic conditions typically 10 mM tartrate and 40 mM phthalate, pH about 5 to about 7 are used. For radiolabeling in basic conditions typically 10 mM glycine, pH about 8 to about 10, is used. The buffer may also contain a number of excipients and/or stabilizers including NaCl, inositol, glucoheptonate, or the like.

The peptide of this invention is reacted with a medically useful metal ion. The medically useful metal ion may be radioactive and generate gamma rays, beta particles, or positrons which are converted into gamma rays upon collision with electrons. Alternatively, the medically useful metal ion may be paramagnetic or supramagnetic. The medically useful metal ion may used in diagnostic imaging procedures including gamma scintigraphy, specific photon emission computerized tomography, positron emission tomography or magnetic resonance imaging.

Particularly useful metal ions can be found in the group consisting of elements 26–30 (Fe, Co, Ni, Cu, Zn), 33–34 (As, Se), 42–50 (Mo, Tc, Ru, Rh, Pd, Ag, Cd, In, Sn) and 75–85 (Re, Os, Ir, Pt, Au, Hg, Tl, Pb, Bi, Po, At). Isotopes of the elements Tc, Re, and Cu are particularly applicable for use in diagnostic imaging and radiotherapy. The isotope $^{99m}$Tc is particularly applicable for use in diagnostic imaging. Other radionuclides with diagnostic or therapeutic applications include $^{62}$Cu, $^{64}$Cu, $^{67}$Cu, $^{97}$Ru, $^{105}$Rh, $^{109}$Pd, $^{186}$Re, $^{188}$Re, $^{198}$Au, $^{199}$Au, $^{203}$Pb, $^{211}$Pb and $^{212}$Bi. The type of medically useful metal ion depends on the specific medical application. The medically-useful metal ion is selected to have a higher order of binding than the positively charged-transition metal ion used to stabilize the metal binding sequences. Radioisotopes of Tc are of significant interest, and particularly $^{99m}$Tc. In the case of $^{99m}$Tc, the peptides are reacted with sodium pertechnetate which has been treated with a reducing agent to generate Tc with a lower oxidation state. The product of the reaction between the metal ion and the peptide is a complex of the metal ion and the peptide. For example, the following structures could result from use of the invention, using Tc labeling of peptides containing metal-ion binding domains consisting of Cys and His groups as an example:

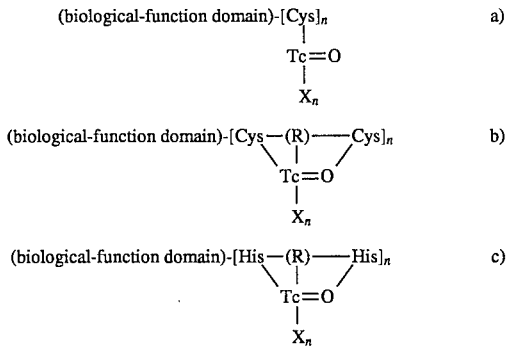

wherein R is an amino acid sequence containing from 0 to about 20 amino acids and $X_n$ is an anion, such as a halogen (e.g. fluoride or chloride), or a solvent molecule, such as water. In the foregoing, the biological-function domain is a peptide sequence including at least the amino acids YIGSR.

The resulting Tc-peptide bond should have a sufficiently high bond strength to minimize the exchange of the radionuclide to transferrin and serum albumin. The complex should be thermodynamically stable under varying physiological conditions and exhibit acceptable toxicological properties.

Most stannous reductions are performed at a pH of from about 5 to about 7. With amino acid side chains in a solution below pH 7, the basic amino acids are positively charged, the acidic amino acids are largely negatively charged, the alcoholic amino acids are neutral, and methionine is neutral. Since reduced technetium binds more readily to neutral hydrogen donors rather than positively charged hydrogen donors, at the pH range 5 to 7 only Cys and His are optimal $^{99m}$Tc binding site candidates. For both Cys and His, radiolabeling yields are dependant on pH, and are theoretically optimal at or near the $pK_a$.

It is also possible to administer the YIGSR-containing peptide, and to perform the actual radiolabeling in vivo. This can be done, for example, using a biotin-avidin system, in which biotin is conjugated to the YIGSR-containing peptide, which is then injected into the patient. A radioisotope-labeled avidin complex is then injected, which binds to the peptide-biotin complex, forming a peptide-biotin-avidin-radiolabel complex, which can be detected by gamma scintigraphy or other detection means. This method presents certain advantages, in that maximum clearance and target binding parameters can be attained. To use this system, for example, it is possible to employ Biotin-HPDP (Pierce Chemical Co.), a cleavable, sulfhydryl-reactive biotinylation reagent. The YIGSR-containing peptide is dissolved in a 100 mM borate buffer pH 8.0 to a final concentration of 1 mg/ml, and biotin-HPDP at 1 mg/ml is added. The solution is mixed and incubated for 1 hour, and the biotinylated peptide separated from unconjugated materials by molecular sieve chromatography over Sephadex G-25. Avidin or strepavidin can be directly iodinated with $^{131}$I by standard methods. Alternatively, avidins can be conjugated to chelating agents such as DTPA or other agents which introduce thiols into the protein, and radiolabeled with $^{99m}$Tc. For use in vivo, the biotinylated peptide is injected intravenously and allowed to localize and clear from the general circulation, a time period generally of from 1 to 2 hours. Radiolabeled avidin is then injected; the radiolabeled avidin binds to the biotin, and consequently localizes the disease lesion.

The peptides of the invention can be:
a) naturally-occurring,
b) produced by chemical synthesis,
c) produced by recombinant DNA technology,
d) produced by biochemical or enzymatic fragmentation of larger molecules,
e) produced by methods resulting from a combination of a–d, or
f) produced by any other means for producing peptides.

By employing synthesis, the preferred means of production, it is possible to introduce various amino acids which do not naturally occur along the chain, modify the N- or C-terminus, and the like, thereby providing for greater lifetime of the peptide, improved stability and formulation, resistance to protease degradation, and the like. The peptides can also include peptide fragments, polypeptides and other like structures, generally consisting of a sequence of amino acids. The peptides can also include fragments of laminin, a basement membrane glycoprotein, including specifically fragments of the polypeptide chain of laminin containing the adhesive sequence YIGSR. The laminin may itself be natural or produced by any means. For the most part, the peptides of this invention comprise fewer than 60 amino acids, and preferably fewer than 30 amino acids, and most preferably ranging from about 10 to 30 amino acids. The term "peptide" as used throughout the specification and claims is intended to include all of the foregoing.

The product resulting from the methods set forth herein can be used for both medical applications and veterinary applications. Typically, the product is used in humans, but may also be used in other mammals. The term "patient" is intended to denote a mammalian individual, and is so used throughout the specification and in the claims. The primary applications of the invention involve human patients, but the invention may be applied to laboratory, farm, zoo, wildlife, pet or sport animals.

The product may be used to monitor or treat normal or abnormal tissues and metabolic events characterized by accumulation of cells with receptors for YIGSR-containing peptides, which accumulations will generally produce a photon-abundant area using most imaging modalities, particularly those involving detection of gamma rays. Most commonly, the product will be used to detect accumulations of platelets. There are a number of clinical conditions in which there are platelet accumulations; these include venous thrombosis, arterial thrombosis, left ventricular thrombosis, pulmonary embolism, inflammatory response secondary to myocardial infarction, endocarditis, bypass graft occlusion, aneurysms, prosthetic arterial graft platelet accumulation or occlusion, cerebral embolism or hemorrhage, traumatic injury with hemorrhage, gastrointestinal hemorrhage, and thrombosis secondary to catheters and other implanted devices.

In Rhodes BA and Zamora PO, U.S. patent application Ser. No. 07/816,477, now U.S. Pat. No. 5,460,785 entitled *Direct Labeling of Antibodies and Other Proteins with Metal Ions*, a method is taught in which a protein substrate, including peptides, containing monosulfides or disulfide bonds is labeled with a medically useful metal ion by the following method:
a) incubating the protein with a reducing agent to reduce some or all of the disulfide bonds to thiolate groups, or to maintain monosulfides as thiolate groups;
b) removing excess reducing agent from the protein substrate containing thiolate groups;
c) adding a source of Sn (II) agent to the thiolate-containing protein preparation in an amount sufficient to form Sn (II)-containing and sulfur-containing complexes; and,
d) adding a medically useful metal ion whereby the metal ion displaces the Sn (II) in the Sn (II)-containing and sulfur-containing complexes and the metal ion and thiolate-containing protein form metal ion-containing and sulfur-containing complexes.

This invention also teaches that it is possible to chemically modify the protein by the introduction of a monosulfide or disulfide bonds. A protein, even though it may not natively contain monosulfides or disulfide bonds, with attached or complexed disulfide bonds can be labeled. The discussions therein pertaining to medically useful metal ions are also appropriate for use with peptides described herein which contain cysteine or penicillamine, and thus contain one or more disulfide bonds or one or more monosulfides. Accordingly, the teachings of this application are incorporated herein by reference.

In Rhodes BA, U.S. patent application Ser. No. 07/840, 076, now U.S. Pat. No. 5,277,892 entitled *Leukostimulatory Agent for In Vivo Leukocyte Tagging*, the use of a variety of leukostimulatory substances, including lectins, peptides and immunoglobulins, labeled or to be labeled with medically useful metal ions, is taught. These teachings, which also involve labeling through disulfide bonds or monosulfides, are specifically applicable to peptides containing cysteine or penicillamine. According, the teachings of that application are incorporated herein by reference.

In Zamora PO and Rhodes BA, U.S. patent application Ser. No. 07/840,077, now U.S. Pat. No. 5,443,816 entitled *Peptide-Metal Ion Pharmaceutical Preparation and Method,* the use of peptide-based metal-ion labeled compositions as pharmaceuticals is taught, together with methods of labeling peptides, proteins and other similar substances with radiometals, paramagnetic metals and other medically useful metal ions. This invention also teaches that peptides containing a biological-function domain and a medically useful metal ion-binding domain can be labeled with medically useful metal ions for use in diagnosis and treatment of a variety of pathologic conditions. Specific medically useful metal-ion labeled peptides for detection of thrombus, cancer, infection and inflammation are provided, including peptides containing the sequence YIGSR. Accordingly, the teachings of this application are incorporated herein by reference.

In Zamora PO, U.S. patent application filed concurrent herewith, entitled *IKVAV Peptide Radiopharmaceutical Applications,* the use of peptides useful for lung imaging, and preferably containing a biological-function domain which includes the sequence Ile-Lys-Val-Ala-Val (IKVAV) and a medically useful metal ion-binding domain are labeled with medically useful metal ions for use in a variety of diseases and pathologic conditions, and particularly diagnostic imaging of diseases and pathologic conditions of the lung, is taught. Accordingly, the teachings of that application are incorporated herein by reference.

The metal ion-binding domain of the peptide involves one or more amino acids containing sulfur, nitrogen or oxygen which is available for binding, or which can be made available for binding to metal ions. Commonly used amino acids include Cys, Pen and His, or any combination of them. The simplest case takes the form
$(R_1)$-$[Cys]_n$-$(R_2)$
wherein $[Cys]_n$ is the medically useful metal ion-binding domain and n is typically a number between 1 and about 6; and $R_1$ and $R_2$ are each an amino acid sequence containing from 0 to about 20 amino acids, with at least $R_1$ and $R_2$ including the biological-function domain. In this and all related forms, it should be noted that $R_1$ and $R_2$ are interchangeable; either can contain the biological-function domain, the biological-function domain may include part or all of both $R_1$ and $R_2$, and the biological-function domain may constitute only a portion of the amino acid sequence in either $R_1$ or $R_2$. The order of components for these purposes can be varied, so that $(R_1)$—$[Cys]_n$-$(R_2)$, $(R_2)$-$[Cys]_n$-$(R_1)$, $[Cys]_n$-$(R_2)$-$(R_1)$, $[Cys]_n$-$(R_1)$-$(R_2)$ and the mirror images of the last two orderings are all equivalent, even though the resulting peptides may significantly differ in other aspects. A representative example of this form is the sequence
Cys-Asp-Pro-Gly-Tyr-Ile-Gly-Ser-Arg
in which the Cys is $[Cys]_n$ wherein n is 1, Tyr-Ile-Gly-Ser-Arg (YIGSR) is the biological-function domain ($R_1$) and the remainder of the sequence is ($R_2$), so that the structure of the sequence is $[Cys]_n$-$(R_2)$-$(R_1)$.

Other forms of the same general configuration include
$(R_1)$-$[Cys$-$(R_2)$-$Cys]_n$-$(R_3)$,
$(R_1)$-$[Cys$-$(R_2)$-$Pen]_n$-$(R_3)$,
$(R_1)$-$[His$-$(R_1)$-$Cys]_n$-$(R_3)$,
$(R_1)$-$[His$-$(R_2)$-$Pen]_n$-$(R_3)$,
and $(R_1)$-$[His$-$(R_2)$-$His]_n$-$(R_3)$,
wherein the sequence [. . . ]$_n$ is the medically useful metal ion-binding domain with n typically being a number between 1 and about 6; and $R_1$, $R_2$ and $R_3$ are each an amino acid sequence containing from 0 to about 20 amino acids, with at least one of $R_1$, $R_2$ and $R_3$ including the biological-function domain which includes at least the sequence YIGSR. Here too the ordering is irrelevant to the functional description; for example, $(R_3)$-$[His$-$(R_2)$-$Cys]_n$-$(R_1)$, $(R_1)$-$(R_3)$-$[His$-$(R_2)$-$Cys]_n$, $(R_3)$—$(R_1)$-$[His$-$(R_2)$-$Cys]_n$, mirror images of the foregoing two orderings, all orderings in which the positions of His and Cys are reversed, and orderings in which the biological-function domain is present in any of the three regions $R_1$, $R_2$ and $R_3$, any portion of the three regions $R_1$, $R_2$ and $R_3$, or any combination of the three regions $R_1$, $R_2$ and $R_3$, are all equivalent to the third configuration listed above, $(R_1)$-$[His$-$(R_2)$-$Cys]_n$-$(R_3)$. Each of the other foregoing configurations can be similarly described.

In one preferred embodiment of the method for labeling peptides of the configurations set forth above, the following method can be employed:
a) adding a source of positively-charged transition metal, most preferably a Sn (II) agent, to the peptide containing amino acids comprising sulfur, nitrogen or oxygen which is available for binding, or which can be made available for binding to metal ions, in an amount sufficient to allow the positively-charged transition metal to undergo a replacement reaction, thereby forming transition metal-containing and sulfur-, nitrogen- or oxygen-containing complexes, or some combination thereof; and, b) adding a medically useful metal ion whereby the metal ion displaces the transition metal in the transition metal-containing and sulfur-, nitrogen- or oxygen-containing complexes and the metal ion and peptide form metal ion-containing and sulfur-, nitrogen-, or oxygen-containing complexes.

The preferred transition metal is Sn (II); useful sources of Sn (II) include stannous tartrate, stannous glucoheptonate, stannous gluconate, stannous phosphonate, stannous chloride, and stannous fluoride. The selection of the source of Sn (II) and its final concentration depends on the intended medical application of the peptide, the nature of the peptide, the relative and absolute number of thiolate groups and the metal ion to be used. In one embodiment stannous tartrate is used at a concentration of 1.25 mM. The stannous tartrate is prepared in a buffer composed of 10 mM tartrate and 40 mM phthalate, pH 5.6, and is added to peptide to yield a final concentration of 1 mg/ml peptide solution.

Sn (II) can be stabilized by use of carboxylic acids, such as acetate, citrate, phthalate and tartrate. A wide range of dicarboxylic acids, known to those skilled in the art, may be similarly used to stabilize the Sn (II) and/or to act as a buffer. If the phthalate and tartrate are in molar excess relative to the Sn (II), then these dicarboxylic acids also stabilize the medically useful metal ion in a form which can react with the peptide. In one embodiment, tartrate and phthalate are used in the Sn (II) agent at concentrations of 10 mM and 40 mM, respectively.

Similarly, the Sn (II) and the medically useful metal ion may be stabilized by free amino acids used singly or in combination with other agents. The type of amino acid used and the specific concentration depends on the nature of the peptide and its intended use. In one embodiment, glycine is used at a concentration of 0.1–10 mM, and in another, histidine is used at a concentration of 0.1–10 mM.

The peptide may be stored in bulk form or in unit dose form after addition of the Sn (II) or other transition metal. For example, in one embodiment the peptide is stored at −20° C. in vials after introduction of the Sn (II). Methods used in lyophilization of peptides are known to those skilled in the art. Either frozen or lyophilized preparations may be maintained for an indefinite period before labeling by the addition of the medically useful metal ion.

In both the frozen and lyophilized storage forms, excipients may be added to the peptide to minimize damage which can arise from ice-crystal formation or free-radical formation. The type of excipient and the concentration depends on the nature of the peptide and the intended use. In one embodiment, glycine and inositol are used as excipients in lyophilized preparations.

A typical lyophilized preparation made by the embodiments set forth above would, upon rehydration, contain 10 mM tartrate, 40 mM phthalate, 22 μg of Sn (II), 500 μg of peptide, 2 mg/ml of glycine, and 2 mg/ml of inositol. To label with a medically useful metal ion, a typical lyophilized preparation is hydrated by the addition of a solution containing 0.9% NaCl (U.S.P.) or water for injection (U.S.P.) and the medically useful metal ion. Alternatively, it is possible to hydrate the lyophilized preparation, and to add the metal ion in a subsequent step. If a frozen preparation is used, it is thawed and allowed to come to room temperature, and a solution containing the medically useful metal ion is then added. The nature and amount of the medically useful metal ion and the specific reaction conditions depend on the isotopic nature of the metal, and the intended medical application. In one embodiment, $^{99m}$Tc is added in the form of pertechnetate ion in a solution of 0.9% NaCl. The $^{99m}$Tc is typically incubated for up to 30 minutes to insure completion of the reaction with the peptide, after which the radiolabeled preparation can be directly used in medical applications.

In the embodiment in which $^{99m}$Tc is used, the Sn (II) is present in the peptide-containing solution in sufficient excess to alter the oxidation state of the Tc ion such that it can bind to ionizable groups. Similar approaches may be used to lower the oxidation state of other medically useful metal ions for subsequent binding to ionizable groups. The type of the metal ion, its isotopic nature, and concentration would depend on the intended medical application.

It is also possible to construct a peptide wherein the biological-function domain contains the sequence YIGSR and the peptide further contains a metal ion-binding domain including one or more disulfide bonds. In that case, it is necessary to first reduce the disulfide bond or bonds. In a preferred method, the following steps are employed:

a) incubating the peptide with a reducing agent to reduce some or all of the disulfide bonds to thiolate groups;
b) removing excess reducing agent from the peptide substrate containing thiolate groups;
c) adding a source of Sn (II) agent to the thiolate-containing peptide preparation in an amount sufficient to form Sn (II)-containing and sulfur-containing complexes; and,
d) adding a medically useful metal ion whereby the metal ion displaces the Sn (II) in the Sn (II)-containing and sulfur-containing complexes and the metal ion and thiolate-containing peptide form metal ion-containing and sulfur-containing complexes.

The order of the steps may be altered, and the method will still produce metal ion-labeled peptides. Accordingly, the claims are not limited to the order of steps presented therein. Specifically, it is possible, and in some cases advantageous, to add the Sn (II) to form Sn (II)-containing and sulfur-containing complexes prior to removing excess reducing agent from the peptide substrate. In this way, oxidation of thiolate groups or reformation of disulfide bonds and other cross-linkages is immediately minimized.

Different configurations of peptides with one or more disulfide bonds are possible, and can be labeled as set forth herein. The most common example is the form

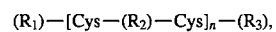

$$(R_1)-[Cys-(R_2)-Cys]_n-(R_3),$$

wherein $[Cys-(R_2)-Cys]_n$ is the medically useful metal ion-binding domain, which can appear in the amino acid sequence from 1 time to about 6 times; and $R_1$, $R_2$ and $R_3$ are each amino acid sequences containing from 0 to about 20 amino acids, with at least one of the amino acid sequences $R_1$, $R_2$ and $R_3$ comprising the biological-function domain YIGSR. Other peptide configurations in which reducible disulfide bonds are present are also included in this method. These include the substitution of Pen for one or both Cys amino acids, as well as the modification of a native Met to allow it to form a disulfide bond. The biological-function domain can appear in any one of $R_1$, $R_2$ and $R_3$, and can also span more than one region, so that the biological-function domain may comprise, for example, $R_2$ and $R_3$, or some portion of $R_2$ and $R_3$. Any one or more of the regions $R_1$, $R_2$ and $R_3$ may contain no amino acids.

Numerous reducing agents have been described and are known to those skilled in the art. Particularly useful types of reducing agents include 2-mercaptoethanol; 1,4-dithiotheitol; 2,3-dihydroxybutane-1,4-dithiol; 2-aminoethanethiol HCl; 2-mercaptoethylamine; thioglycolate; cyanide; cysteine; reduced glutathione; Sn (II); Cu (I); and Ti (II). The reducing agent may be dissolved in a solute or may be attached to a solid phase. Reducing agents attached to a solid phase are commercially available, and methods for their use are known to those skilled in the art. The degree to which the peptide requires disulfide bond reduction depends on the nature of the peptide and its intended medical application. Generally speaking, milder reduction conditions and shorter incubation periods are normally employed than are required to reduce disulfide bonds in proteins or complex polypeptides, such as antibodies. In any event, reduction is halted before excessive fragmentation of the peptide or loss of the biological-function of the peptide occurs.

In one specific embodiment, Sn (II) is used as a reducing agent at a concentration of 5 mM. In this embodiment the Sn (II) is dissolved in a buffer composed of approximately 10 mM tartrate and 40 mM phthalate, pH 5.5, and the Sn (II) buffer admixed with a peptide substrate at a concentration of 8.3 mg/ml. The reduction reaction is allowed to proceed for a period of time at room temperature, three hours having been employed successfully with some peptides containing a single disulfide bond, after which time the reaction is terminated by removing excess Sn (II) ions by molecular sieve chromatography. One means of molecular sieve chromatography employs Sephadex G-25, with the chromatography gel pre-equilibrated, and the peptide eluted in 0.9% NaCl or other suitable buffer.

Removal of the reducing agent, whether Sn (II) or some other reducing agent, can be accomplished by a variety of suitable means, including such methods as dialysis, ultrafiltration, positive-pressure membrane filtration, precipitation, preparative high performance liquid chromatography, affinity chromatography, other forms of chromatography and preparative isoelectric focusing. Many of the reducing agents contain thiols, which if present in the final labeling mixture, can complex with the medically useful metal ion. Such complexes can have severe and unknown side effects if administered in vivo. Additionally, some reducing agents exhibit unacceptable toxicity. Thus removal of the reducing agent both limits the degree of reduction to that desired, as well as providing for increased utility and safety of the labeled preparation by removal of toxic or otherwise undesirable reducing agents.

Thiolate groups in reduced peptides are highly reactive and can interact to reform disulfide bonds. The use of Sn (II) is believed to minimize the reformation of disulfide bonds. Sources of Sn (II) include stannous tartrate, stannous glucoheptonate, stannous gluconate, stannous phosphonate, stannous chloride, and stannous fluoride. The selection of the source of Sn (II) and its final concentration depends on the intended medical application of the peptide, the nature of the peptide, the relative and absolute number of thiolate groups and the metal ion to be used. In one embodiment stannous tartrate is used at a concentration of 1.25 mM. The stannous tartrate is added to the peptide after removal of the peptide-reducing agent. The stannous tartrate is prepared in a buffer composed of 10 mM tartrate and 40 mM phthalate, pH 5.6, and is added to peptide to yield a final concentration of 1 mg/ml peptide solution.

The invention is further illustrated by the following non-limiting examples.

EXAMPLE 1

Preparation of Peptide Kits for $^{99m}$Tc Labeling

Laminin-derived peptide of the sequence CDPGYIGSR ($H_2N$-Cys-Asp-Pro-Gly-Tyr-Ile-Gly-Ser-Arg) was obtained commercially (Bachem, Inc.) as lyophilized powder and used without additional purification. The N-terminal thiolate associated with the Cys residue was used as the metal ion-binding domain for subsequent labeling with reduced $^{99m}$Tc.

Peptide labeling kits were prepared aseptically using nitrogen-purged solutions, and whenever feasible under an atmosphere of nitrogen. To prepare the peptide labeling kits, the peptide was dissolved to a final concentration of 1.4 mg/ml in chilled, nitrogen-purged 10 mM tartrate/40 mM phthalate buffer, pH 5.6 (P/T buffer) containing 2% maltose. The peptide and P/T buffer solution was then mixed (7:3) with P/T buffer containing 1.25 mM stannous tartrate. Aliquots (typically 0.5 ml containing 500 Bg of peptide) were then sterile filtered through a 0.22 micron filter, and dispensed into individual vials. The head space of each vial was purged with nitrogen, the vials stoppered and crimped, and stored frozen at −70° C.

EXAMPLE 2

$^{99m}$Tc Labeling of Peptide Kits

To radiolabel, a vial of the preparation of Example 1 was removed from the freezer and allowed to come to room temperature. The labeling reaction was initiated by the addition of 0.5–2.0 mCi of $^{99m}$Tc (sodium pertechnetate in saline). Radiochemical analysis was begun 30 minutes after the introduction of the pertechnetate.

EXAMPLE 3

Radiochemical Analysis by Chromatography

To determine the relative amount of $^{99m}$Tc bound to a given peptide preparation, aliquots of the $^{99m}$Tc-labeled preparations were analyzed by molecular sieve HPLC, reverse phase chromatography, and thin layer chromatography.

Molecular sieve HPLC was performed using a 7.5×300 mm TSK G3000SW column preceded with a TSK-SW 7.5×75 mm guard column (TosoHaas, Philadelphia, Pa.) at a flow rate of 1 ml/minute phosphate buffered saline (0.01M phosphate, pH 7.0, containing 0.15M NaCl), with a UV and radioisotope detector in series. The preparation of Example 1 eluted at 13.9 minutes with a high chromatographic recovery (greater than 95%). In control studies, pertechnetate eluted at 17.8 minutes with essentially quantitative chromatographic recovery.

For reverse-phase analysis, Sep-Pak Cle mini-columns (Millipore Inc., Bedford, Mass.) were used as reverse-phase adsorbents to evaluate the binding of $^{99m}$Tc to the peptides. The columns were rinsed with 10 ml of 100% ethanol followed by 10 ml of 0.001% HCl. Aliquots of 100 µl of the test sample were loaded onto the column and the unbound material eluted with 10 ml of 0.001% HCl. The column was then serially eluted with a graded series of 10 ml solutions aqueous ethanol (10%, 20%, 30%, 40%, 50%, 60%, and 100%). The radioactivity in each eluant fractions (0.001% HCL-100% ethanol) was determined by counting an aliquot (20 µl) of each fraction in a gamma scintillation counter. The columns themselves were also counted, after allowing an appropriate time for decay. All counts were corrected for decay and the amounts of radioactivity in each fraction expressed as a percentage of the total radioactivity assayed. Reverse-phase chromatography using $C_{18}$ mini-columns eluted with a graded series of ethanol confirmed $^{99m}$Tc binding to the peptides (Table 1).

TLC was used to measure the amount of peptide-bound (and unbound) $^{99m}$Tc and the amount of radiolabeled aggregate/colloid. Both measurements involved the use of ITLC-SG (Gelman Sciences, #61886) chromatography paper, cut into 1.5×10 cm strips and activated by heating for 30 minutes at 110° C., as per the manufacturer's instructions. After heating, the strips were stored at room temperature until use.

Peptide-bound $^{99m}$Tc in the radiolabeled preparations was measured using TLC in 85% aqueous methanol using ITLC-SG strips. The solvent separated the soluble, unbound $^{99m}$Tc (which migrates with the solvent front) from $^{99m}$Tc bound to the peptide (which remains at the origin). Percentage of unbound $^{99m}$Tc was expressed as CPM in the origin half of the strip divided by the total CPM, with all measures corrected for background.

Thin layer chromatography of the preparation of Example 1 in saline over heat-activated silica-gel coated cellulose (ITLC-SG paper) showed essentially all radioactivity associated with the peptide ($R_f$=0). The preparations did not contain significant amounts of unbound $^{99m}$Tc as pertechnetate or $^{99m}$Tc-tartrate ($R_f$=1.0).

TABLE 1

Elution of $^{99m}$Tc-peptide preparation of Example 1 from C$_{18}$ reverse-phase columns by increasing concentrations of ethanol. Tartrate was used in the kits as a $^{99m}$Tc transfer agent. In the absence of peptide tartrate retains $^{99m}$Tc, and its elution is provided here as a reference.

| Percent EtOH in Eluent | PERCENTAGE OF TOTAL RADIOACTIVITY ASSAYED | |
|---|---|---|
| | $^{99m}$Tc-Tartrate | $^{99m}$Tc-Peptide |
| 0% | 90.9% | 0.0% |
| 10% | 2.2% | 8.9% |
| 20% | 1.6% | 58.7% |
| 30% | 0.8% | 19.5% |
| 40% | 0.5% | 4.9% |
| 50% | 0.8% | 1.3% |
| 60% | 0.5% | 1.8% |
| 100% | 1.1% | 0.9% |
| On Column | 1.6% | 4.0% |

EXAMPLE 4

Biodistribution in Rodents

The biodistribution of the $^{99m}$Tc-peptide of Example 1 was evaluated in adult female Swiss-Webster mice (approximately 19 g) at selected times (10, 30, and 120 minutes) after injection into the tail vein. Each experimental group was composed of at least five animals, with each animal receiving 0.1 ml containing 5 µg of peptide (1 µCi/µg). Animals were sacrificed by Halothane overdose, and selected organs dissected, weighed, and associated radioactivity determined. Data were analyzed using a computer program specifically designed for $^{99m}$Tc-labeled preparations. The percent dose per organ for blood, bone, and muscle were calculated assuming 7, 8.2, and 40% of total body weight, respectively, for these tissues.

TABLE 2

Biodistribution of $^{99m}$Tc-peptide of Example 1 in normal Swiss-Webster mice at selected times after injection. All values are the mean ± standard deviation. n = 6 for all data points except 120 minutes, where n = 5.

| ORGAN | INJECTED DOSE/ORGAN | | |
|---|---|---|---|
| | 10 MINUTES | 30 MINUTES | 120 MINUTES |
| blood | 7.8 ± 1.5 | 2.4 ± 0.3 | 1.5 ± 0.2 |
| stomach | 0.5   0.1 | 0.2   0.1 | 0.1   0.1 |
| sm. intestine | 4.2   1.6 | 7.8   0.9 | 1.9   0.2 |
| appendix | 0.3   0.1 | 0.1   0.0 | 2.0   0.8 |
| lg. intestine | 0.6   0.4 | 0.2   0.0 | 1.0   0.3 |
| liver | 4.9   1.3 | 3.4   0.4 | 1.3   0.0 |
| spleen | 0.1   0.0 | 0.0   0.0 | 0.0   0.0 |
| kidneys | 11.8   1.9 | 7.7   0.6 | 5.2   0.8 |
| heart | 0.3   0.13 | 0.1   0.0 | 0.0   0.0 |
| lungs | 0.6   0.1 | 0.2   0.0 | 0.1   0.0 |
| bone | 2.9   0.4 | 0.9   0.1 | 0.6   0.2 |
| muscle | 14.4   1.5 | 3.7   1.1 | 2.1   0.5 |
| thyroid | 0.1   0.0 | 0.0   0.0 | 0.0   0.0 |

Some studies involved pre-incubation of the $^{99m}$Tc-peptide in whole blood prior to injection and determination of biodistribution (Table 3). In these studies, whole human blood was obtained from a healthy adult male donor and collected into Vacutainer tubes containing EDTA. After mixing to insure proper dissolution of the EDTA, approximately 2.5 ml of the whole blood was removed and mixed with 0.25 ml of $^{99m}$Tc-peptide. The mixture was allowed to incubate 30 minutes at room temperature. After 30 minutes, aliquots of 0.1 ml were injected into the tail vein of the mice. The amount of radioactivity in the circulation for $^{99m}$Tc-peptide of Example 1 pre-incubated in whole blood was similar to that in animals receiving $^{99m}$Tc-peptide without incubation in blood.

TABLE 3

Biodistribution in normal Swiss-Webster mice of $^{99m}$Tc-peptide of Example 1 after a 30 minute preincubation in whole blood. All values are the mean ± standard deviation. n = 5 for all data points.

| ORGAN | % INJECTED DOSE/ORGAN | |
|---|---|---|
| | 10 MINUTES | 30 MINUTES |
| blood | 9.9 ± 4.7 | 3.7 ± 0.7 |
| stomach | 0.6   0.1 | 0.3   0.0 |
| liver | 5.3   1.0 | 4.3   1.3 |
| spleen | 0.1   0.0 | 0.1   0.0 |
| kidneys | 11.4   2.7 | 9.0   1.4 |
| heart | 0.3   0.1 | 0.1   0.0 |
| lungs | 0.7   0.3 | 0.3   0.0 |
| bone | 3.4   1.2 | 1.2   1.2 |
| muscle | 15.8   4.5 | 5.7   1.9 |
| thyroid | 0.1   0.1 | 0.0   0.0 |

The clearance rates of the $^{99m}$Tc-peptide of Example 1 was evaluated in adult female Sprague-Dawley rats at 2 hours after injection. Each experimental group was composed of three animals. Each animal was anesthetized with ketamine and the bile duct and bladder were cannulated. Blood was collected over various periods of time from the jugular vein. The $^{99m}$Tc-peptide cleared very rapidly from the plasma of rats, with a clearance rate of 2.6 ml/minute. At two hours, 31.2±9.1% of the injected doses had cleared through urine, while bile clearance at the same time point was 6.9±0.3%. In biodistribution studies, the highest amount of radioactivity was found in the kidneys, and is consistent with the rat clearance data. No major accumulation of radioactivity was found in any organ examined (other than kidney), and at later times (2 and 4 hours post injection) no re-distribution of the radiolabel was noted.

EXAMPLE 5

In Vitro Binding to Platelets and Colon Carcinoma Cells

The peptide of Example 1, labeled with $^{99m}$Tc as in Example 2, was used to measure relative binding to colon carcinoma cells, platelets and induced clots. In these studies, $^{99m}$Tc-human IgG was used as a control. Measurements were expressed as a percent of final counts per minute, using the control $^{99m}$Tc-human IgG as 100%.

For studies of LS-174T binding, cells were grown in cell culture. For studies of binding to platelets and induced clots, normal whole human blood was collected in citrated buffer, and the platelet-rich plasma collected by differential centrifugation. Platelets were either used directly, or were clotted. For clot studies, 2 drops of a saturated solution of calcium chloride and magnesium chloride were added to 1 ml of platelet-rich plasma, clots were allowed to form, rinsed in buffer, and placed in phosphate buffered saline containing 1% bovine serum albumin. In all experiments, the $^{99m}$Tc-peptide and $^{99m}$Tc-human IgG preparations were allowed to incubate for 30 minutes at 37° C. with the carcinoma cells, platelets and clots. For cells and platelets, separation preparatory to counting was by centrifugation; for clots, separation was by washing.

TABLE 4

Binding of $^{99m}$Tc-YIGSR-containing peptide and $^{99m}$tc-human IgG to LS-174T colon carcinoma cells

| Sample | Final Binding (CPM) | Percent of Control |
|---|---|---|
| EXPERIMENT ONE (n = 3) | | |
| $^{99m}$Tc-Human IgG (control) | 40,568 ± 11,275 | 100% |
| $^{99m}$Tc-YIGSR-Peptide | 98,194 ± 30,422 | 242% |
| EXPERIMENT TWO (n = 3), REPEAT OF EXPERIMENT ONE | | |
| $^{99m}$Tc-Human IgG (control) | 91,198 ± 41,545 | 100% |
| $^{99m}$Tc-YIGSR-Peptide | 276,977 ± 21,828 | 304% |

TABLE 5

Binding of $^{99m}$Tc-YIGSR-containing peptide and $^{99m}$Tc-human IgG to human platelets and clots

| Sample | Final Binding (CPM) | Percent of Control |
|---|---|---|
| EXPERIMENT ONE (n = 3), PLATELETS IN PLATELET-RICH PLASMA | | |
| $^{99m}$Tc-Human IgG (control) | 76,986 ± 12,173 | 100% |
| $^{99m}$Tc-YIGSR-Peptide | 243,269 ± 43,838 | 315% |
| EXPERIMENT TWO (n = 3), CLOTS | | |
| $^{99m}$Tc-Human IgG (control) | 28,331 ± 7,233 | 100% |
| $^{99m}$TC-YIGSR-Peptide | 159,763 ± 22,314 | 564% |

In other experiments, the peptide of Example 1, labeled as in Example 2, was used for in vitro binding studies. In these studies, the radiolabeled peptide was incubated for 90 minutes with either 0.5 ml of whole blood clots, using from 0.4 to 50 µg of radiolabeled peptide, or with approximately $10^7$ platelets, using from 2 to 200 µg of radiolabeled peptide. These studies showed a dose-response relationship between the amount of radiolabeled peptide and the blood clots or platelets.

EXAMPLE 6

In Vivo Localization in Induced Clots

Experimental jugular thrombi were induced in adult Fisher 344 rats using 20 µg/0.1 ml of thrombin. Studies were conducted using quantitative whole body autoradiography. The peptide of Example 1, labeled with $^{99m}$Tc as in Example 2, was injected intravenously, with whole body autoradiography conducted 90 minutes after injection. Whole body autoradiography showed rapid clearance of radioactivity through or by kidneys, and to a lesser degree, through the biliary system. Significant accumulation of radioactivity was noted in the induced jugular thrombi, with a thrombus to muscle ratio of 15:1.5, and a thrombus to blood ratio of 3:1.

EXAMPLE 7

Modified YIGSR-containing Peptide with Multiple Recognition Units

A peptide with a longer sequence to improve blood retention and repeated sequences of YIGSR to improve binding to platelets is synthesized. Synthesis is done by solid-phase synthesis techniques using t-butyloxycarbonyl (Boc) protected amino acids added sequentially to a Gly-resin ester, followed by reverse-phase HPLC purification. The sequence of the peptide is as follows:

CDGGGYIGSRGGYIGSRGGGDC
(Cys-Asp-Gly-Gly-Gly-Tyr-Ile-Gly-Ser-Arg-Gly-Gly-Tyr-Ile-Gly-Ser-Gly-Gly-Gly-Arg-Cys)

The foregoing peptide has a purity of greater than 98% as determined by reverse phase HPLC. The amino acid composition is confirmed by amino acid analysis.

The foregoing peptide is dissolved directly in nitrogen-purged 10 mM/40 mM tartrate/phthalate buffer, pH 5.5 (P/T buffer). The dissolved YIGSR-containing peptide is adjusted to a final concentration of 1 mg/ml in 10 mM P/T buffer containing 40 µg/ml of stannous tartrate and stored frozen, under a nitrogen atmosphere, in 5 cc amber serum-vials until labeled. For labeling, a vial is allowed to come to room temperature and $^{99m}$Tc, as sodium pertechnetate, is added. The labeling reaction is allowed to proceed for 30 minutes. Essentially all of the $^{99m}$Tc is complexed to the peptide as determined by HPLC analysis.

EXAMPLE 8

Modified YIGSR-containing Peptide with Multiple Recognition Units and D-Amino Acid Sequences A peptide containing D-amino acid sequences is used to confer metabolic resistance for in vivo use. The peptide of Example 7 is modified to include such D-amino acid sequences. Synthesis is done by solid-phase synthesis techniques using t-butyloxycarbonyl (Boc) protected amino acids added sequentially to a Gly-resin ester, followed by reverse-phase HPLC purification. The sequence of the peptide is as follows:

(D)-Cys-(D)-Asp-Gly-Gly-Gly-(D)-Tyr-Ile-Gly-(D)-Ser-Arg-Gly-Gly-(D)-Tyr-Ile-Gly-(D)-Ser-Gly-Gly-Gly-Asp-(D)-Cys

The forgoing peptide has a purity of greater than 98% as determined by reverse phase HPLC. The amino acid composition is confirmed by amino acid analysis.

The foregoing peptide is dissolved directly in nitrogen-purged 10 mM/40 mM tartrate/phthalate buffer, pH 5.5 (P/T buffer). The dissolved YIGSR-containing peptide is adjusted to a final concentration of 1 mg/ml in 10 mM P/T buffer containing 40 µg/ml of stannous tartrate and stored frozen, under a nitrogen atmosphere, in 5 cc amber serum-vials until labeled. For labeling, a vial is allowed to come to room temperature and $^{99m}$Tc, as sodium pertechnetate, is added. The labeling reaction is allowed to proceed for 30 minutes. Essentially all of the $^{99m}$Tc is complexed to the peptide as determined by HPLC analysis.

EXAMPLE 9

Preparation of Lyophilized YIGSR-containing Peptide Radiolabeling Kits

YIGSR-containing peptide radiolabeling kits of Examples 1, 7 or 8 are prepared, with the addition of glycine and inositol as excipients. The kits are then individually vialed and lyophilized.

EXAMPLE 10

Animal Localization Studies

The kits of Examples 1, 7, 8 or 9 are used in animal localization studies of induced pulmonary thromboembolism in adult Swiss-Webster mice with collagen/adrenaline-induced pulmonary embolism. Immediately prior to use in the studies, the animals are anesthetized by an intramuscular injection of pentobarbital. Each mouse is injected with 0.1 ml of saline containing 10 µg of collagen and 5 µg of adrenaline. This treatment results in the aggregation of circulating platelets and the subsequent lung deposition of emboli. Animals so treated exhibit 20–30% thrombocytopenia relative to control animals. Control animals receive sham injections of 0.1 ml saline. After an appropriate amount of time to allow for the development of pulmonary thromboembolism (5–15 minutes), the animals are injected with $^{99m}$Tc-YIGSR-containing peptides of Examples 1, 7, 8, or 9, and 10 and 30 minute biodistribution studies are performed.

EXAMPLE 11

Diagnostic Imaging of Thrombosis

A kit of Examples 1, 7, 8 or 9 is used in to localize thromboembolism in a patient. After radiolabeling with $^{99m}$Tc as in Example 2, the $^{99m}$Tc-peptide is injected intravenously. Starting immediately upon injection, the patient is imaged, using conventional gamma scintigraphy or SPECT imaging, and is imaged at 30 minute intervals thereafter. Sites of thromboembolism will appear as photon-rich image locations by scintigraphy consistent with circulatory distribution.

All of the foregoing are merely illustrative, and other equivalent embodiments are possible and contemplated. The preceding examples can be repeated with similar success by substituting the generically or specifically described reactants and/or operating conditions of this invention for those used in the preceding examples.

Although the invention has been described in detail with reference to these preferred embodiments, other embodiments can achieve the same results. Variations and modifications of the present invention will be obvious to those skilled in the art and it is intended to cover in the appended claims all such modifications and equivalents. The entire disclosures of all applications, patents, publications and other references cited above are hereby incorporated by reference.

What is claimed is:

1. A peptide-based pharmaceutical composition suitable for administration to a patient comprising:
   a peptide comprising, in part, a biological-function domain which comprises the peptide sequence YIGSR and further comprising, in part, a medically useful metal ion-binding domain; and
   a metal ion labeling agent.

2. The peptide-based pharmaceutical composition of claim 1 wherein said peptide comprising a biological-function domain which comprises the peptide sequence YIGSR and a medically useful metal ion-binding domain is selected from the group consisting of:

$(R_1)$-$[Y_1]_n$-$(R_2)$,
   $(R_1)$-$[Y_1$-$(R_2)$-$Y_1]_n$-$(R_3)$, and
   $(R_1)$-$[Y_1$-$(R_2)$-$Y_2]_n$-$(R_3)$
   wherein the medically useful metal ion-binding domain comprises a member selected from the group consisting of $[Y_1]_n$, $[Y_1$-$(R_2)$-$U_1]_n$ and $[Y_1$-$(R_2)$-$Y_2]_n$ in which n is a number between 1 and about 6 and $Y_1$ and $Y_2$ are amino acids comprising at least one element selected from the group consisting of sulfur, nitrogen or oxygen which is available or can be made available for binding to metal ions;
   the biological-function domain comprising the peptide sequence YIGSR further comprises at least one member selected from the group consisting of $R_1$, $R_2$ and $R_3$; and
   those portions of $R_1$, $R_2$ and $R_3$ not comprising the biological-function domain comprising the peptide sequence YIGSR each comprise an amino acid sequence containing from 0 to about 20 amino acids.

3. The peptide-based pharmaceutical composition of claim 1 wherein the medically useful metal ion-binding domain comprises at least one amino acid sequence selected from the group consisting of cysteine, cystine, histidine, penicillamine, deacylated methionine, lysine, arginine, aspartic acid, glutamic acid and tyrosine.

4. The peptide-based pharmaceutical composition of claim 3 wherein said medically useful metal ion-binding domain is selected from the group consisting of $[Cys]_n$,
   $[Cys$-$(R_2)$-$Cys]_n$,
   $[Cys$-$(R_2)$-$Pen]_n$,
   $[His$-$(R_2)$-$Cys]_n$,
   $[His$-$(R_2)$-$Pen]_n$,
   $[His]_n$, and
   $([His$-$(R_2)$-$His]_n$
   wherein n is a number between 1 and about 6; and
   $R_2$ is an amino acid sequence containing from 1 to about 20 amino acids.

5. The peptide-based pharmaceutical composition of claim 1 wherein said metal ion labeling agent comprises a stannous ion agent.

6. The peptide-based pharmaceutical composition of claim 5 wherein said stannous ion agent is present in a solution comprising alkali metal tartrate.

7. The peptide-based pharmaceutical composition of claim 5 wherein the stannous ion agent is present in a solution comprising a dicarboxylic acid.

8. The peptide-based pharmaceutical composition of claim 7 wherein the dicarboxylic acid comprises at least one member selected from the group consisting of phthalate, tartrate and citrate.

9. The peptide-based pharmaceutical composition of claim 5 wherein the stannous ion agent comprises a member selected from the group consisting of stannous tartrate, stannous glucoheptonate, stannous gluconate, stannous phosphonate, stannous chloride, and stannous fluoride.

10. The peptide-based pharmaceutical composition of claim 1 wherein the composition further comprises a medically useful metal ion.

11. The peptide-based pharmaceutical composition of claim 1 wherein the composition is lyophilized.

12. The peptide-based pharmaceutical composition of claim 1 wherein the peptide comprising a biological-function domain which comprises the peptide sequence YIGSR and a medically useful metal ion-binding domain is a peptide comprising the sequence CDPGYIGSR.

* * * * *

UNITED STATES PATENT AND TRADEMARK OFFICE
CERTIFICATE OF CORRECTION

PATENT NO. : 5,567,408
DATED : October 22, 1996
INVENTOR(S) : Paul O. ZAMORA

It is certified that error appears in the above-indentified patent and that said Letters Patent is hereby corrected as shown below:

Title page, [75] Inventor: Change "Puerta De Hierro, N.M." to --Albuquerque N.M.--

Signed and Sealed this

Eighth Day of April, 1997

Attest:

BRUCE LEHMAN

*Attesting Officer*   Commissioner of Patents and Trademarks